United States Patent [19]

Funke et al.

[11] 4,359,312

[45] Nov. 16, 1982

[54] RECIPROCATING PUMP FOR THE PULSATION-FREE DELIVERY OF A LIQUID

[75] Inventors: Herbert Funke, Krailling; Hans-Jurgen Riggenmann, Munich, both of Fed. Rep. of Germany

[73] Assignee: Zumtobel KG, Lindau, Fed. Rep. of Germany

[21] Appl. No.: 933,832

[22] Filed: Aug. 15, 1978

[51] Int. Cl.³ .............................................. F04B 49/00
[52] U.S. Cl. ....................................... 417/18; 417/539
[58] Field of Search ........................... 417/18, 22, 539

[56] References Cited

U.S. PATENT DOCUMENTS

| | | | |
|---|---|---|---|
| 1,723,874 | 8/1929 | Longe | 417/539 |
| 2,010,377 | 8/1935 | Sasson | 417/539 |
| 3,781,907 | 12/1973 | Gerber | 417/42 |
| 3,816,029 | 6/1974 | Bowen | 417/539 |
| 3,847,507 | 11/1974 | Sakiyama | 417/22 |
| 3,917,531 | 11/1975 | Magnussen | 210/101 |
| 3,932,667 | 1/1976 | Ball | 417/390 |
| 4,053,902 | 11/1977 | Skafuenstedt | 417/489 |
| 4,127,360 | 11/1978 | Carpenter | 417/539 |
| 4,128,476 | 12/1978 | Rock | 210/101 |
| 4,131,393 | 12/1978 | Magnussen | 417/45 |
| 4,137,011 | 1/1979 | Rock | 417/22 |
| 4,233,156 | 11/1980 | Tsukada | 210/101 |

FOREIGN PATENT DOCUMENTS

| | | | |
|---|---|---|---|
| 2446005 | 4/1976 | Fed. Rep. of Germany | 417/426 |
| 2010112 | 11/1976 | Fed. Rep. of Germany | 417/900 |
| 336 | of 1913 | United Kingdom | 91/491 |

Primary Examiner—William L. Freeh
Attorney, Agent, or Firm—Fitzpatrick, Cella, Harper & Scinto

[57] ABSTRACT

A piston pumping system is disclosed having a pair of piston pumps operated by plungers with roller follows which ride in rotary cam plate grooves. The grooves are arranged such that the delivery of each pump overlaps the suction of the other pump. Means are provided to sense any pulsations in pressure to change the cam speed during the precompression phase of operation and means are provided to sense delivery pressure and to adjust cam plate speed during the interval between the initial phase of delivery and the end of the precompression stroke.

9 Claims, 16 Drawing Figures

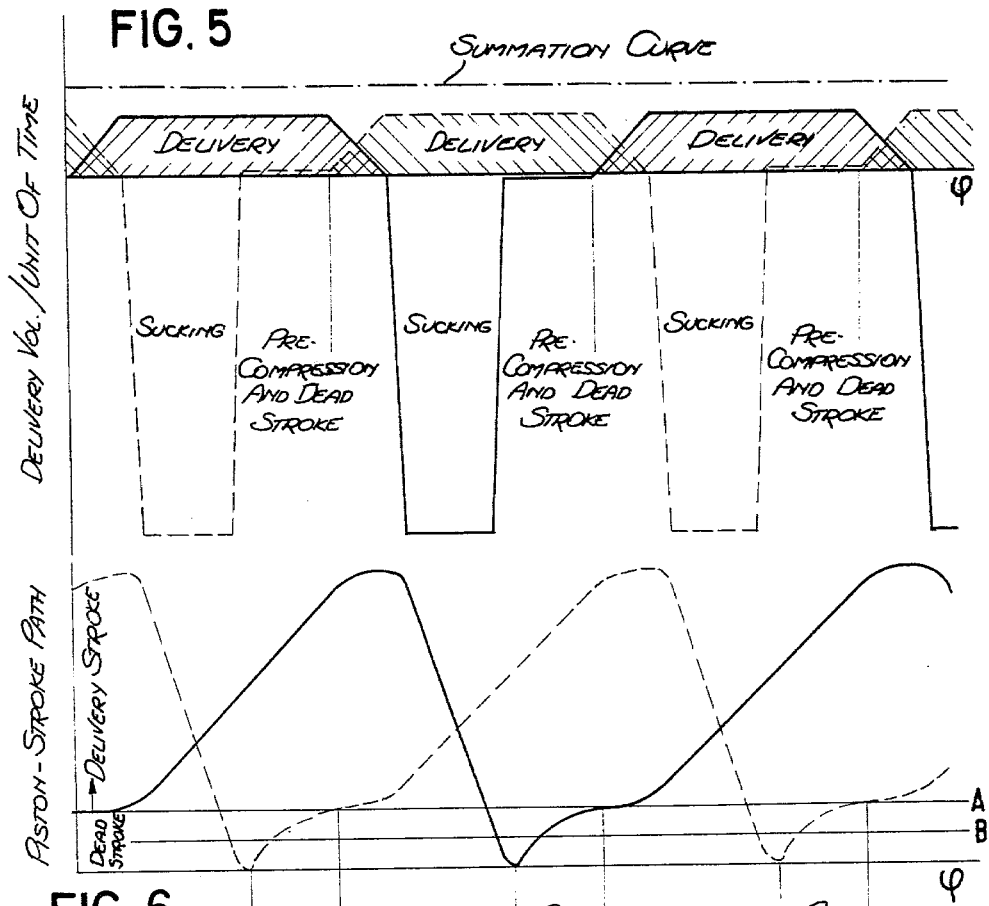
FIG. 5
FIG. 6
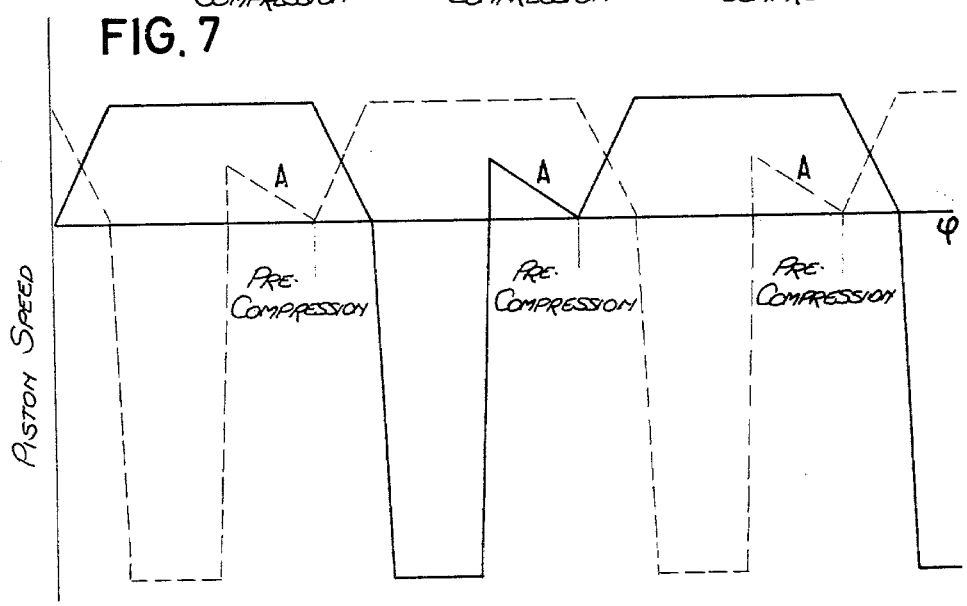
FIG. 7

RECIPROCATING PUMP FOR THE PULSATION-FREE DELIVERY OF A LIQUID

BACKGROUND OF THE INVENTION

1. Field of the Invention

This invention concerns a reciprocating piston pump for the pulsation-free delivery of a liquid with the use of at least two cylinders connected in parallel on their discharge side, of which one in each instance sucks and the other delivers, in which the pistons working in said cylinders are controlled by cam means, and in which each piston, for the purpose of compensating for the compressibility of the liquid, is caused to perform a precompression stroke before each delivery stroke.

Reciprocating piston pumps of the aforesaid type are employed to supply liquids for use in chromatographic investigations.

2. Description of the Prior Art

In a known reciprocating piston pump as disclosed in the German Specification No. 2,446,805 laid out for public inspection the length of the precompression stroke is adjusted to the compressibility of the liquid to be pumped in order to ensure pulsation-free delivery of the liquid. For the purpose of permitting such an adjustment to be effected, this known reciprocating piston pump is provided with adjusting screws constituting stop means for piston tappets each of which co-operates with a disc cam associated therewith. Said adjusting screws may each be moved into a stopping position in which they are adapted, as a suction stroke is being performed, to intercept the piston tappets before they reach their rearward limit positions so as to preclude any further motion in a rearward direction. Thus, within a predetermined portion of each revolution, the disc cams will come out of contact with their respective piston tappets. The said portion may be considered as being equivalent to a precompression stroke. However, when the operating conditions, i.e. for example the temperature or the viscosity of the liquid or the pressure against which pumping is to be done, and/or the composition of the liquid to be pumped are altered, manual or automatic readjustment will have to be effected. This, in turn, will result in the liquid throughput to be changed.

OBJECT OF THE INVENTION

It is a primary object of the present invention to provide a reciprocating piston pump of the type aforesaid in which both freedom from pulsations and constancy of throughput are attained by varying only a single operating parameter.

SUMMARY OF THE INVENTION

This object is accomplished pursuant to the invention by keeping the length of the precompression stroke constant, by reducing to a predetermined value the rotary speed of the rotary drive means at the beginning of liquid delivery, by again increasing said rotary speed to its normal value up to the end of the precompression stroke, and by reducing the rotary speed throughout this sequence of events as a function of the additional amount of liquid delivered as a result of precompression.

The invention is based on the following considerations: When a liquid is being pumped which has a very high compressibility, or when a very high back pressure has to be overcome by the pump, there exists the possibility that liquid delivery will not start before the end of the precompression stroke has been reached. In such a case, the normal value of the rotary speed of the rotary drive is employed throughout the pumping process. However, if the compressibility of the liquid and the operating conditions are such that delivery of liquid will start even before the end of the precompression stroke, the rotary speed of the rotary drive is reduced to the said predetermined value at the start of delivery and increased again to its normal value by the end of the precompression stroke so that the liquid volume which is prematurely delivered during this period by the piston performing its precompression stroke is compensated for by a reduction of the liquid volume delivered by the other piston. When the rotary speed is reduced, the fact should be taken into consideration that any such reduction will also result in a reduction of the liquid volume delivered by the piston which is performing its precompression stroke. The amount of the reduction depends on the point at which delivery starts within the precompression stroke and is determined by a definite function when a cam plate of predetermined shape is employed. This mode of compensation makes it possible to provide for pulsation-free delivery of the liquid. Hereinbelow it will be termed "primary control".

Where the liquid is allowed to expand upon leaving the pump, precompression will result in an increase in the amount of liquid delivered. This increase in pump throughput is compensated for by the fact that the rotary speed of the rotary drive is reduced proportionally throughout the sequence of events produced by said primary control action. The constancy of throughput thus obtained is termed "secondary control". Primary control as well as secondary control is effected by varying the speed of the rotary drive, said speed thus being the only operating parameter to be controlled.

Until the end of the precompression stroke is reached, the rotary speed of the rotary drive may again be increased to its normal value in accordance with different yet definite functions requiring the employment of suitable cam plates of different shape. It has been found that maximum simplicity may be obtained in practice by providing for a uniform increase in speed, i.e. in accordance with a linear function.

In an advantageous embodiment of the invention use may be made of a double-grooved cam plate the grooves of which positively co-operate with suitable cam followers. This will afford an additional advantage over the said known reciprocating piston pump in that it is not necessary to provide restoring springs for the pistons. Springs fatigue in use; and their elimination, according to the present invention prolongs the operating life and the maintenance intervals of the pump. Besides that it is possible to employ a rotary drive of lower power so that power losses are reduced.

Primary control of the reciprocating piston pump may be practically effected by means of a precompression stroke indicator indicating the beginning of the precompression stroke, a rotary-position indicator which indicates the momentary rotary or angular position of the cam plate, and a pressure-pulse discriminator connected with a pressure measuring instrument, by means of which it can be determined whether a pressure pulse is due to overcompensation or undercompensation, an operating program storage for the rotary drive in which are stored a plurality of operating programs determining, for various specified angular positions of the cam plate between the beginning and the end of the precompression stroke, a correspondingly different pattern of the reduction in operating speed of the cam plate between the specific angular position associated in each instance with the cam plate and the end of the precompression stroke, and an operating program selector, coupled with the pressure-pulse discriminator, which according to whether the pressure-pulse discriminator indicates overcompensation or undercompensation, causes the program storage to activate a program in which the assigned specific angular position is at a smaller or greater distance from the starting point of the precompression stroke than in the previously selected operating program. The operating programs differ at least in respect of the degree to which the rotary speed of the rotary drive of the cam plate is reduced and in respect of the distance in time between the point at which the reduction begins and the point at which the normal rotary speed is again attained. There exists a definite relation between the degree of the reduction and the said distance in time or interval.

For the purpose of providing the said secondary control it is possible to provide, between the rotary drive for the cam plate and the operating program storage, a compression computer which is adapted to receive from the operating program storage the operating program selected and to receive, from the precompression stroke indicator, via the pressure pulse discriminator and the operating program selector, information as to the interval between the beginning of the precompression stroke and the beginning of liquid delivery, said compression computer being adapted, taking into consideration certain parameters of the reciprocating piston pump fed to the computer, to effect a proportional reduction of the rotary speed determined by the selected operating program, such reduction being effected throughout the sequence of events.

There may be connected between the compression computer and the rotary drive a multiplier serving to multiply the operating program modified by the compression computer by a factor capable of being selected by means of a throughput preselector. For the purpose of providing a rotary drive capable of being rapidly and accurately controlled, it is proposed to employ an electric motor and to couple with the electric motor a tachometer generator designed to generate an actual-value signal intended to be transmitted to a servo controller serving to control the electric motor and receiving its desired-value signal from the multiplier.

The precompression-stroke indicator may comprise a signaling element attached to the cam plate and a sensor responsive to the signals produced thereby.

As has been brought out in the introduction, the reciprocating piston pump of this invention is preferably adapted to deliver liquids, but it should be understood that, as a matter of principle, it is also adapted to deliver gases.

An embodiment of the invention is described below, reference being had to the accompanying drawings, in which:

FIG. 5 is a diagram showing the relationship between the delivery volume per unit of time and the angle of rotation of the cam plate for a real compressible fluid to be delivered against a pressure higher than atmospheric pressure, in which is used a cam plate producing the piston stroke pattern of FIG. 6;

FIG. 6 is a diagram showing the relationship between the length of the piston stroke and the angle of rotation of the cam plate with the inclusion of a precompression phase;

FIG. 7 is a diagram showing the relationship between the speed of the piston and the angle of rotation of a cam plate producing the piston stroke pattern shown in FIG. 6;

DETAILED DESCRIPTION OF THE PREFERRED EMBODIMENT

Figure 1:
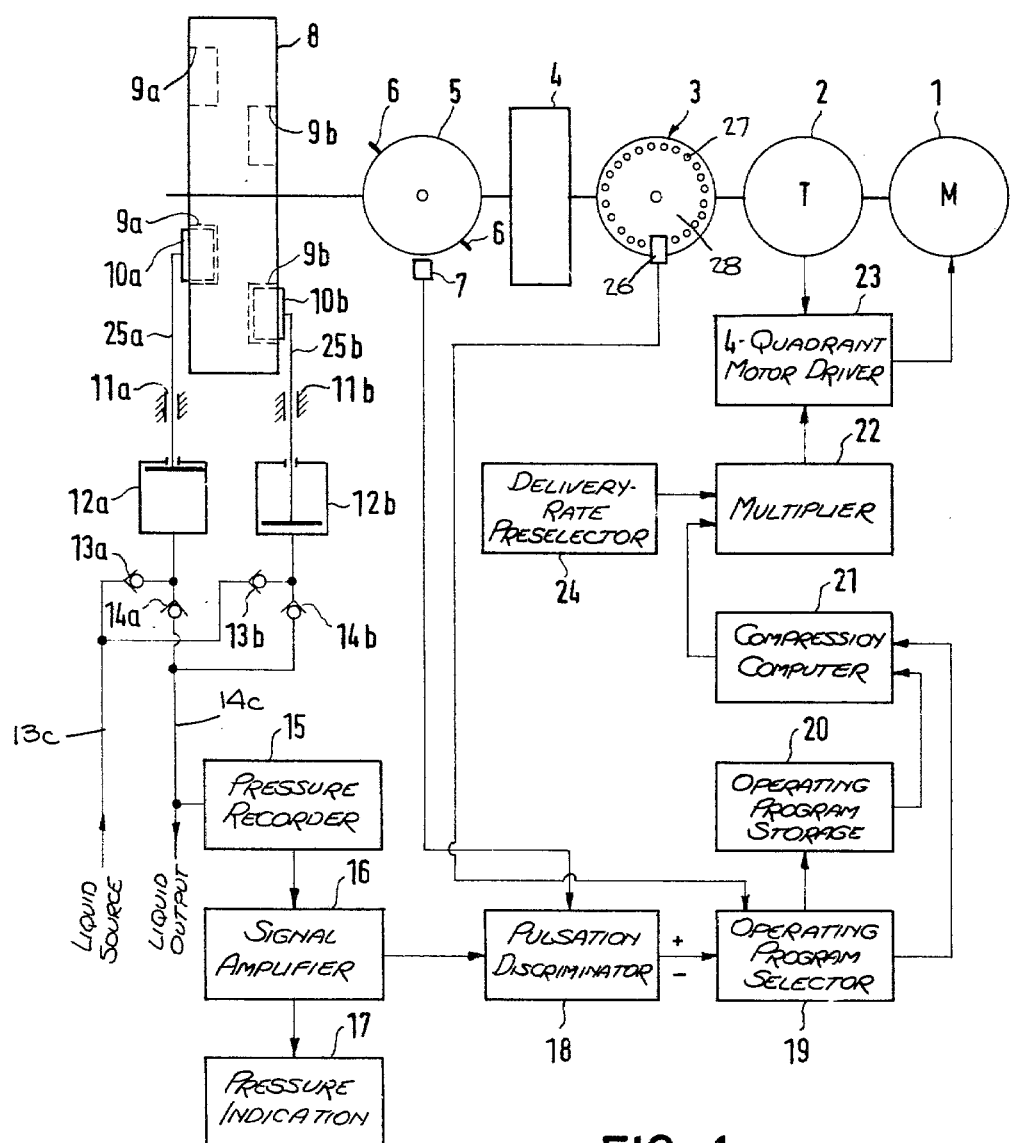
FIG. 1 shows a block diagram of the reciprocating piston pump which, for the purpose of simplifying the following explanation, illustrates only the more important connections between the various blocks.
Figure 10:
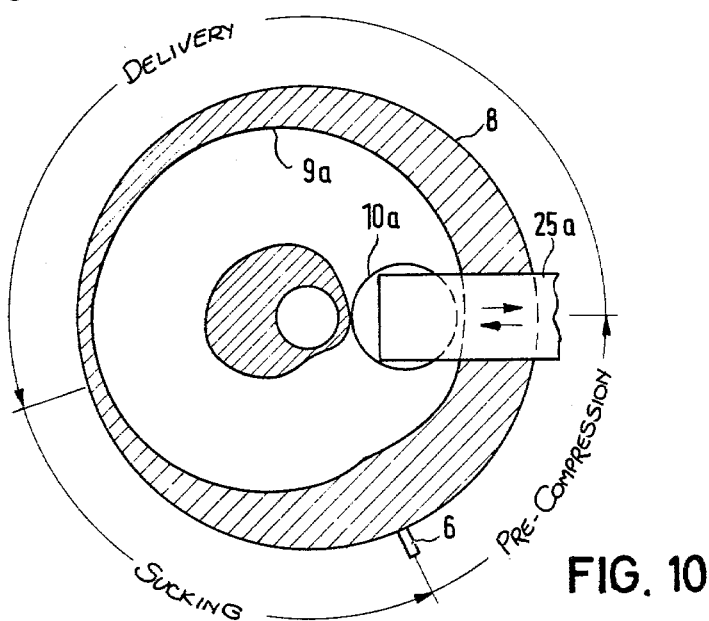
FIG. 10 is a side view of a double-grooved cam plate having a roller and a plunger associated therewith.

The reciprocating piston pump shown in FIG. 1 comprises two cylinders 12a, 12b containing pistons which are controlled by a double-grooved cam plate 8 shown in side view in FIG. 10. The double-grooved cam plate 8 has a groove 9a, 9b on each side. In each groove runs a roller 10a, 10b connected with the corresponding plunger 25a, 25b. Each plunger 25a, 25b is slidably supported in one of two bearings 11a, 11b serving to absorb the loads imposed on the plungers by the cam plate tangentially of the cam tracks.

Either of the cylinders 12a, 12b is connected with an inlet or suction valve 13a, 13b and an outlet or discharge valve 14a, 14b. Both of the inlet valves 13a, 13b are connected to a fluid source; the outlet valves 14a, 14b form the discharge outlet for the fluid to be delivered in a pulsation-free manner.

The common outlet line 14c is connected to a pressure recorder 15 which converts the pressure pulses into electric pulses which are supplied to a signal amplifier 16. The signal amplifier delivers signal data to a pressure indicator 17 which, however, is not necessary for the fundamental operation of the arrangement. In addition, signal amplifier 16 is connected to a pulsation discriminator 18 serving to determine whether the pulses delivered by signal amplifier 16 are due to overcompensation or undercompensation.

Cam plate 8 is driven by an electric motor 1. Mounted on the drive shaft of electric motor 1 is a tachometer generator 2 delivering a signal indicating the actual speed of the motor to a servo controller 23 capable of being operated as a power amplifier. Servo controller 23 is supplied with a signal indicating the desired speed derived from multiplier 22. Servo controller 23 is a four-quadrant motor driver designed to match the speed of motor 1 with the desired value derived from multiplier 22.

Also mounted on the drive shaft of electric motor 1 is an angle-of-rotation indicator 3 designed, upon being rotated, to produce pulses the number of which corresponds to the number of angle increments passed through. Rotary-angle indicator 3 comprises a disc 28 which is provided at its periphery with a set of circumferentially spaced holes 27 located on a circle which is concentric with the axis of rotation. The holes 27 are scanned by means of fork-type light barriers 26.

Cam plate 8 is coupled to motor 1 through a reduction gearbox 4. Mounted on cam plate 8 is a precompression indicator separately shown in FIG. 1 as a disc 5. Disc 5 is provided with at least one signaling element designed to cooperate with a sensor 7 in the form of a fork-type light barrier. In practice, as shown in FIG. 10, indicating element 6 is directly mounted on cam plate 8.

The reciprocating piston pump also includes an operating program storage 20 in which are stored a plurality of operating programs for cam plate 8. The individual operating programs differ from each other in that the speed of rotation of cam plate 8 is, in each case, reduced in relation to its normal value at a different point between the beginning of the precompression phase and the end of the precompression phase and is restored to the normal value by the end of the precompression phase in accordance with a predetermined function. The program to be used is selected by an operating-program selector 19 connected to operating program storage 20. Program selector 19 receives, from pulsation discriminator 18, information as to whether the pulsation detected is due to overcompensation or undercompensation. When the detected pulsation is due to overcompensation, program selector 19 will derive from program storage 20 an operating program in which the reduction of the rotational speed of cam plate 8 takes place at an earlier time after the beginning of the precompression phase than in the preceding program. When, however, the detected pulsation is due to undercompensation, an operating program will be selected in which the reduction of the speed of rotation of cam plate 8 takes place at a later time. Thus, the operating program selected in each instance will take care of the primary control function.

The secondary control function by which constancy of delivery (weight of fluid delivered per unit time) is to be ensured, is effected by a compression computer 21 connected to operating program storage 20 and to operating program selector 19. Compression computer 21 receives, from precompression-stroke indicator 5, 6, 7, via pulsation discriminator 18 and operating program selector 19, information as to the point at which the compression stroke will begin. In addition, compression computer 21 receives, from rotational-position indicator 3 by way of operating program selector 19, information as to the cam plate position angle at which delivery will begin. In the case of a real compressible fluid to be delivered against a pressure higher than atmospheric pressure, delivery always begins before the end of the precompression stroke.

In the case of the cam plate shown in FIG. 10, the cam groove segment along which precompression is effected is of such a length that, when the fluids to be pumped and with the pressures to be overcome by the pump, delivery will in each case begin before the end of the precompression phase.

Compression computer 21 computes a correction factor for the rotary speed of electric motor 1 determined by the selected operating program so that in the case of a real compressible fluid the increase in throughput caused by precompression is compensated for between the beginning of the precompression stroke and the beginning of delivery. In doing this, computer 21 takes into consideration the ratio between the precompression stroke and the total stroke length and the ratio between the dead volume and the displacement volume of cylinders 12a, 12b. The precompression stroke actually utilized is computed by compression computer 21 from the information it receives from operating program selector 19 and from operating program storage 20. Program selector 19 receives its information from the precompression stroke indicator and from angular-position indicator 3.

The operating program corrected by compression computer 21 is fed to multiplier 22, which latter is connected to a delivery rate preselector 24 permitting the desired delivery rate to be selected. Multiplier 22 modifies the operating program inputted thereto in accordance with the delivery rate for which preselector 24 has been set.

The manner in which the reciprocating piston pump of FIG. 1 operates will now be described with reference to the diagrams shown in FIGS. 2 to 9.

Figure 2:
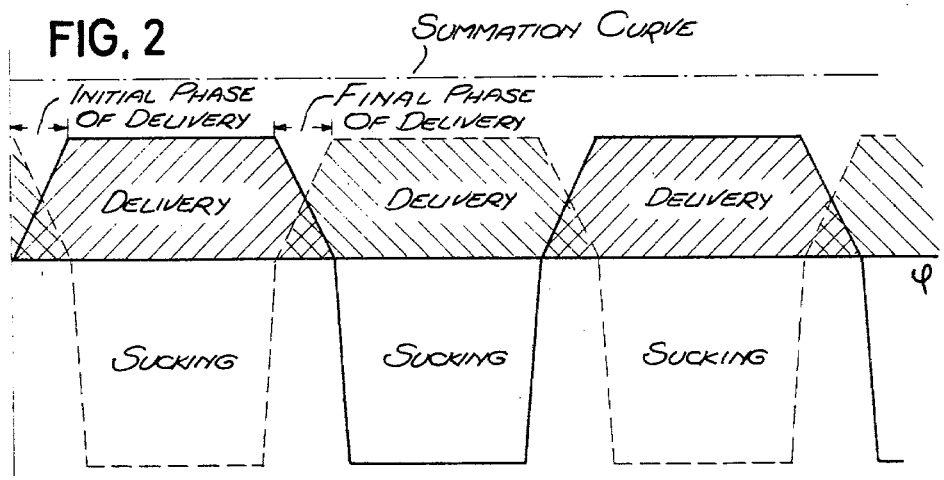
FIG. 2 is a diagram showing the relationship between the delivery volume per unit of time and the angle of rotation of the cam plate for an ideal incompressible fluid.

FIG. 2 shows a delivery diagram for an ideal incompressible fluid. In order to obtain pulsation-free delivery, the initial phase of delivery of one cylinder (diagram in solid lines) and the final phase of delivery of the other cylinder (diagram in broken lines) are caused to overlap so that the summation curve (dot-dash line) shown in FIG. 2 results. A delivery diagram according to FIG. 2 can be obtained with a cam plate in which the piston stroke is related to the angle of rotation in the manner shown in FIG. 3, with the speed of rotation of the cam plate being maintained constant.

Figure 3:
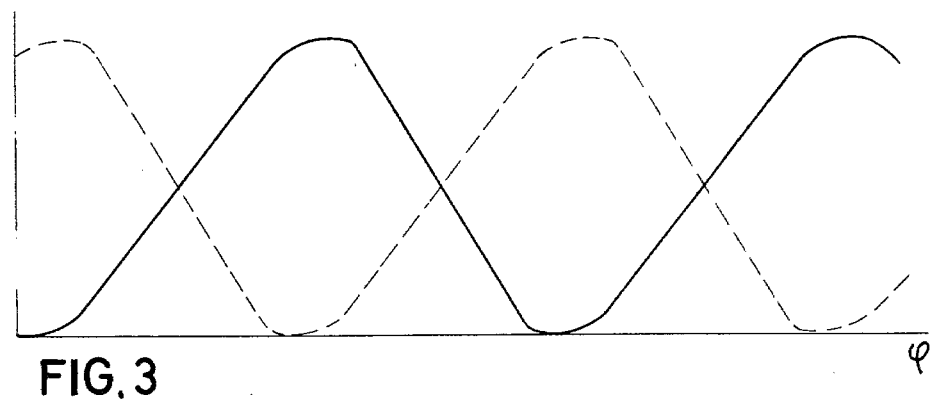
FIG. 3 is a diagram showing the relationship between the length of the piston stroke and the angle of rotation of the cam plate used for controlling the pistons in such a manner that the pump is operated in accordance with the delivery diagram of FIG. 2.
Figure 4:
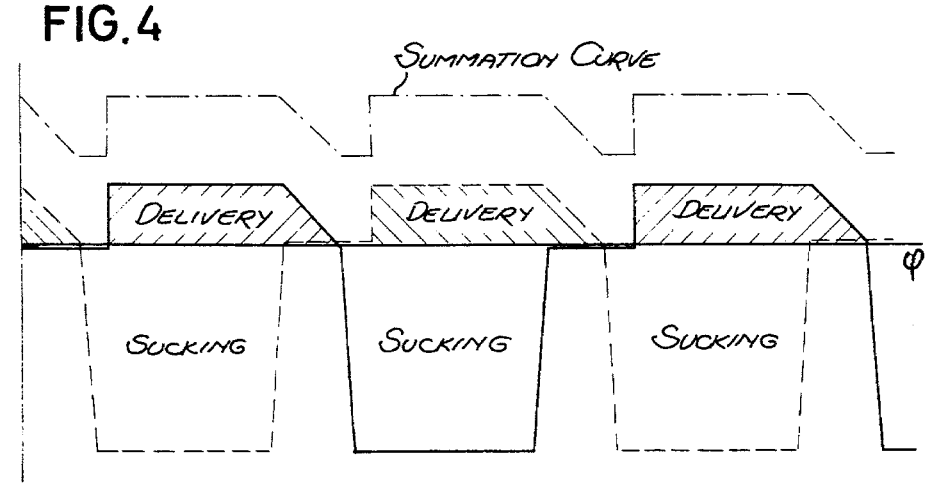
FIG. 4 is a diagram showing the relationship between the delivery volume per unit of time and the angle of rotation of the cam plate for a real compressible fluid to be delivered against a pressure higher than atmospheric pressure, in which is used a cam plate producing the piston stroke pattern of FIG. 3.

When use is made of a cam plate in which the piston stroke is related to the angle of rotation in the manner shown in FIG. 3 and when the speed of rotation of the cam plate is kept constant, the delivery diagram shown in FIG. 4 will be obtained for a real fluid which is compressible and is delivered against a pressure higher than atmospheric pressure. It will be noted from FIG. 4 that there is no longer any overlapping of the delivery actions of the two cylinders so that valleys occur in the summation curve. These valleys are reflected in pressure pulses which are caused by undercompensation.

As shown in FIG. 5 it is now proposed, also in respect of real compressible fluids to be delivered against a pressure higher than atmospheric pressure, to obtain a flat summation curve by again causing the delivery stroke sections to overlap by shortening the suction stroke and by a corresponding precompression within the region gained by shortening the suction stroke. This is possible with a cam plate designed to produce the relationship shown in FIG. 6 between the piston stroke and the angle of rotation. According to FIG. 6 the precompression phase is selected in such a manner that up to the end of the precompression phase the fluid is in practice only compressed without any delivery being effected and that the initial phase of delivery begins after the end of the precompression phase.

The length of the precompression phase has further been dimensioned with regard for that fluid of those to be delivered which has the highest compressibility and with regard for the highest pressure against which delivery is to be effected by the reciprocating piston pump.

FIG. 7 shows the piston speed as a function of the angle of rotation of a cam plate producing the piston stroke pattern shown in FIG. 6. The piston speed in each instance corresponds to the differential quotient of piston stroke length versus angle of rotation. Thus, the curves of FIG. 7 are the differentiated curves of FIG. 6. It will be seen therein that, during the precompression phase, the piston speed is initially increased abruptly and then declines again. However, as shown in FIG. 6, the piston is advanced steadily during this phase so that precompression does actually take place.

If now a fluid is used having a lower compressibility than the one on which the dimensioning of the precompression phase of FIG. 6 was based, or when the pressure against which delivery is to be made is lower than the pressure on which the dimensioning of the precompression phase was based, the initial phase of delivery will begin even before the end of the precompression phase. As shown in FIG. 6, this means that the dead stroke will end already upon line B being reached, with the initial phase of delivery beginning immediately thereafter. The dimensioning of the precompression phase is based on a dead stroke ending at line A.

Figure 8:
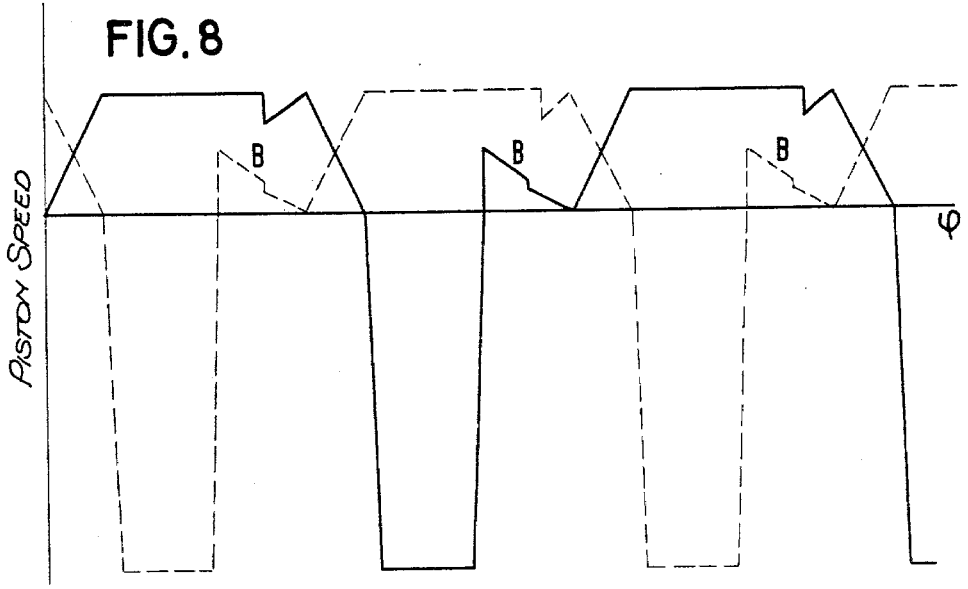
FIG. 8 is a diagram showing the piston speed as a function of the angle of rotation of a cam plate producing a piston stroke pattern corresponding to the diagram of FIG. 6 with the speed of the cam plate being varied in the manner shown in FIG. 9.

With the dead stroke already ending at line B and with the initial phase of delivery following immediately thereafter, maintaining the speed of rotation of the cam plate constant will necessarily result in overcompensation. This means that a pulsation of the fluid delivered will be detected. This effect is counteracted by the rotational speed of the cam plate being reduced between the time at which the initial phase of delivery starts and the time at which the precompression phase ends, this being shown in FIG. 9. This reduction in speed of the cam plate results in a reduction of the delivery volume of the two cylinders as indicated in FIG. 8. It will be understood that compensation is possible in this way, so that a smooth summation curve is again obtained. Cam speed curves solid line a., dashed line b., and dash-dotted line c., illustrate different speeds of the cam plate effecting different amounts of this compensation.

The compensation just described is effected by means of an approximation procedure in which, by successively selecting different operating programs, the time at which the reduction of the rotational speed of the cam plate starts is advanced towards the time at which the initial phase of delivery begins. This approximation is continued until pulsation discriminator 18 no longer reports any pressure pulses to operating program selector 19.

In this connection it should be noted that, with the reciprocating piston pump shown in FIG. 1, use may be made of a simple pressure measuring instrument which need only give a qualitative indication as to whether overcompensation or undercompensation is present. There are no requirements for a specific accuracy of measurement with regard to the quantitative magnitude of the pressure.

Figure 11:
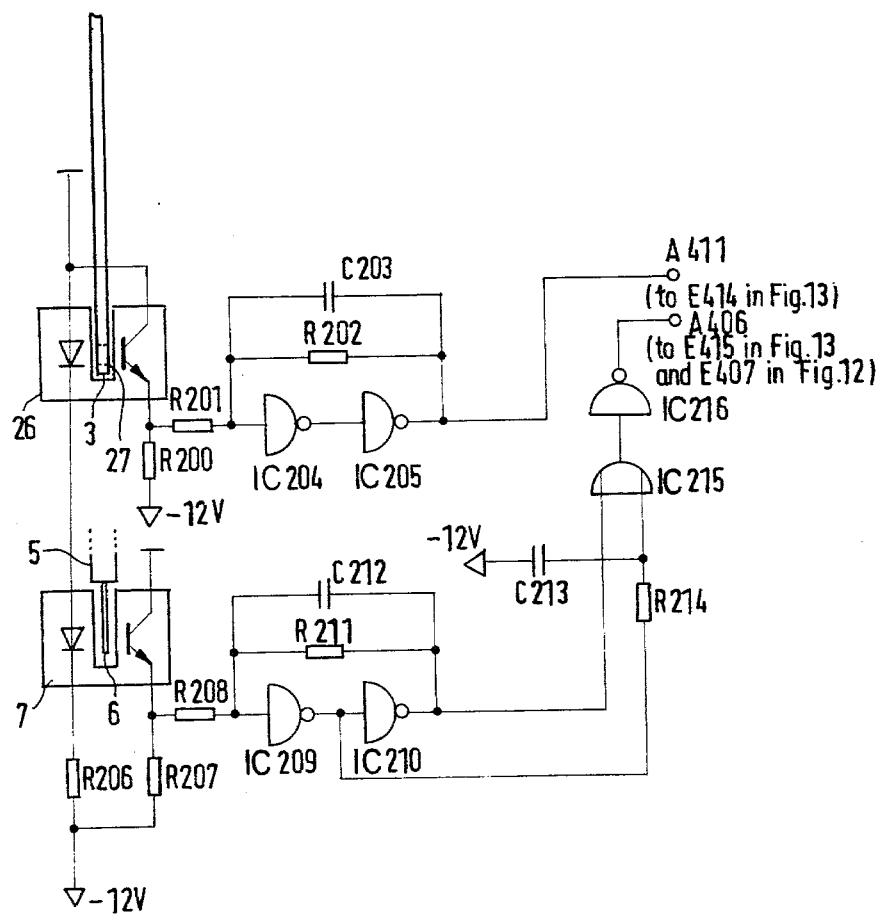
FIG. 11 is a wiring diagram showing details of the rotary-position indicator and the compression-stroke indicator.

As shown in FIG. 11, the fork-type light barrier 26 comprises a light-emitting diode and a phototransistor between which perforated disc 27 is rotated. The light barrier may comprise a barrier manufactured as Type OPB 815 by Optron Inc., a company residing in the U.S.A. One terminal each of the light-emitting diode and the phototransistor is grounded. The other terminal of the phototransistor receives a voltage of $-12$ V via a resistor R200. The output of the phototransistor is transmitted to a Schmitt trigger comprising a resistor R201, a resistor R202, a capacitor C203 and two inverters IC204 and IC205. The output of the Schmitt trigger appears at a terminal A411.

The fork-type light barrier 7 associated with the precompression stroke indicator is identical in construction with the fork-type light barrier 26. The light emitting diode of light barrier 7 is connected to the light emitting diode of light barrier 26. In addition, the light-emitting diode of barrier 7 receives a voltage of $-12$ V via a resistor R206. The phototransistor of light barrier 7 is grounded on one side thereof and receives, at its other terminal, a voltage of $-12$ V via a resistor R207. The output of light barrier 7 is fed to another Schmitt trigger comprising a resistor R208, a resistor R211, a capacitor C212 and two inverters IC209 and IC210.

The output of the last-mentioned Schmitt trigger is transmitted to a positive-edge detector comprising inverter IC210 (also forming part of the last-mentioned Schmitt trigger), an OR element IC215, an inverter IC216, a resistor R214 and a capacitor C213 having a voltage of $-12$ V applied to one of its terminals. The output of this positive-edge detector appears at a terminal A406.

Figure 12:
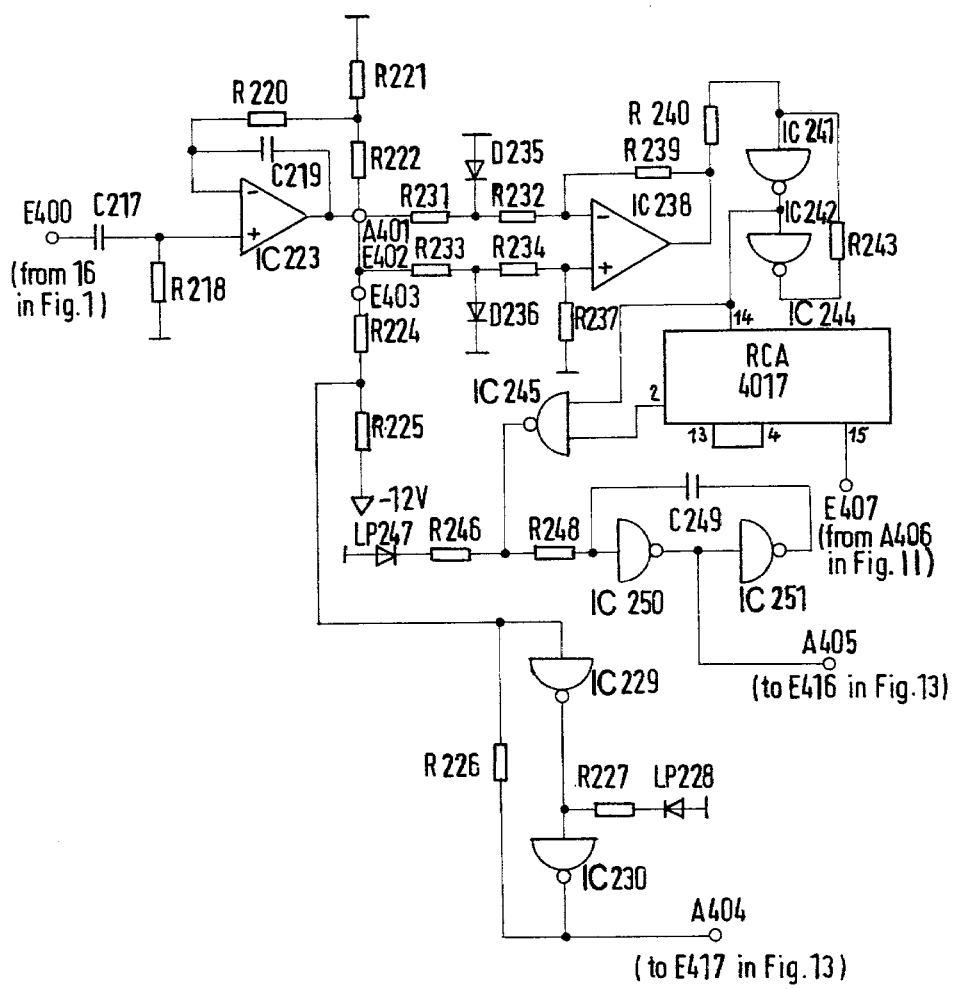
FIG. 12 is the wiring diagram of an embodiment of a pulsation discriminator.

The pulsation discriminator 18 shown in FIG. 12 is designed to detect whether the pulses supplied by signal amplifier 16 are due to overcompensation or undercompensation. For this purpose, the positive input of an operational amplifier IC223 receives, from signal amplifier 16, measuring signals supplied via input terminal E400 and a differentiating element which latter comprises a capacitor C217 and a resistor R218. A feedback connection including a capacitor C219 is provided between the output of operational amplifier IC223 and negative input thereof. In addition, the output of operational amplifier IC223 is grounded via two series-connected resistors R222 and R221. The junction between these two resistors is connected via a resistor R220 to the negative input of operational amplifier IC223. This amplifier is operated in the non-inverting mode. In addition, the output of operational amplifier IC223 is connected to a $-12$ V terminal via two series-connected resistors R224 and R225. Furthermore, the output of operational amplifier IC223 is connected, via two series-connected resistors R231 and and R232, to the negative input of another operational amplifier IC238. Moreover, the positive input of operational amplifier IC238 is connected, via two series-connected resistors R233 and R234, to the output of the first operational amplifier IC223. A diode D235 is connected between the junction of resistors R231 and R232 and ground. Another diode D236 is connected between the junction of resistors R233 and R234 and ground. The positive input of the second operational amplifier IC238 is grounded via a resistor R237. The negative input of operational amplifier IC238 is connected to the output thereof via a resistor R239. In addition, the output of the second operational amplifier is connected via a resistor R240 to the input of an inverter IC241. The output of inverter IC241 is directly connected to the input of another inverter IC242. The output of inverter IC242 is connected to the input of first inverter IC241 by means of a resistor R243. The junction between the two inverters IC241 and IC242 is connected to pin 14 of a counter IC244 in the form of type RCA4017. Pin 14 is also connected to one input of a NAND gate IC245, of which the other input is connected to pin 2 of counter IC244. The two pins 4 and 13 of counter IC244 are interconnected. Pin 15 of counter IC244 is connected to an input terminal E407 which is in turn connected to output A406 of sensor 7.

The output of NAND gate IC245 is, on the one hand, grounded via a resistor R246 and a light-emitting diode LP247, and, on the other hand, connected to the input of an inverter IC250 via a resistor R248. The output of inverter IC250 is connected to the input of another inverter IC251 the output of which is connected, through a capacitor C249, to the input of the first inverter IC250. The junction between the two latter inverters is connected to an output terminal A405 which is, in turn, connected to operating program selector 19 (input terminal E416).

The input of still another inverter IC229 is connected to the junction between the two resistors R224 and R225. The output of inverter IC229 is connected to a further inverter IC230 of which the output is connected, via a resistor R226, to the input of inverter IC229. The junction between the two inverters IC229 and IC230 is grounded through a resistor R227 and a light-emitting diode LP228. The output signal of inverter IC230 is transmitted to an output terminal A404 which is connected to the input terminal E417 of operating program selector 19.

Figure 13:
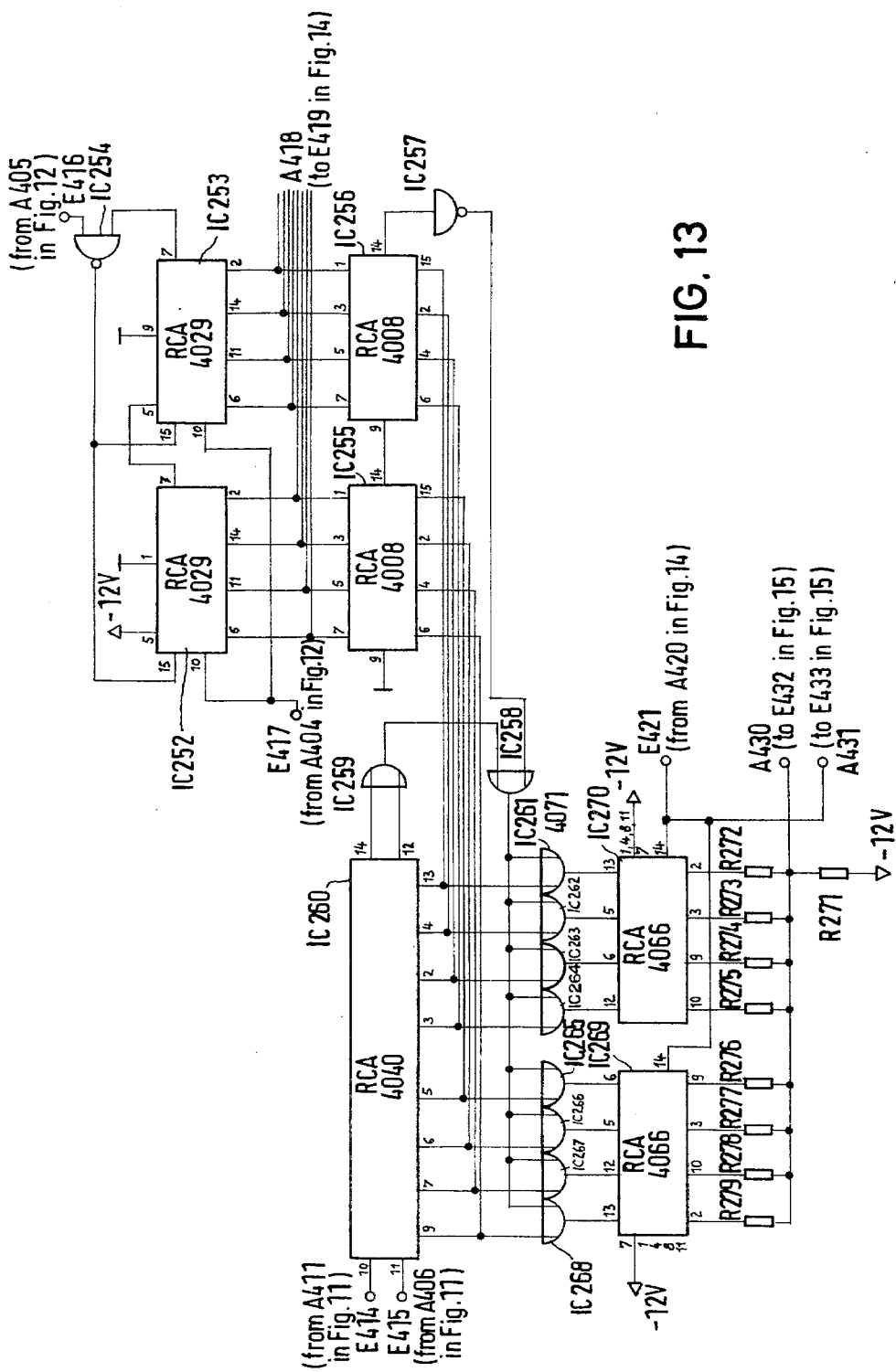
FIG. 13 is the wiring diagram of an embodiment of the operating program selector and the operating program storage means.

As will be seen in the detailed wiring diagram shown in FIG. 13, operating program selector 19 comprises circuit elements IC252 to IC258 and IC261 to IC268. Circuit element IC254 is a NAND gate. Circuit elements IC252 and IC253 are counters, each being of type RCA 4029. Circuit elements IC255 and IC256 are RCA type 4008 four-bit full adders. Circuit element IC257 is an inverter, element IC258 being an OR gate. Also elements IC261 to IC268 are OR gates.

From output terminal A405 of pulsation discriminator 18 a signal is transmitted to input E416 of NAND gate IC254. The other input of IC254 is connected to pin 7 of IC253. The output of IC254 is connected to pins 15 of IC252 and IC253. Pin 5 of IC252 has a voltage of −12 V supplied thereto. Pins 9 of IC252 and IC253 are grounded. Pin 7 of IC252 is connected to pin 5 of IC253. Pins 10 of IC252 and IC253 are connected to an input terminal E417 which is, in turn, connected to output terminal A404 of pulsation discriminator 18.

Pins 6, 11, 14 and 2 of IC252 are respectively connected to pins 7, 5, 3 and 1 of IC255. Pins 6, 11, 14 and 2 of IC253 are respectively connected to pins 7, 5, 3 and 1 of IC256. From each of the pins 6, 11, 14 and 2 of the two IC's 252 and 253 and the corresponding pins of the two IC's 255 and 256 there extends one of several output lines A418 leading to compression computer 21 and to the corresponding input lines E419.

Pin 9 of IC255 is grounded. Pin 14 of IC255 is connected to pin 9 of IC256. Pin 14 of IC256 is connected to the input of IC257, the output of the latter being connected to one input of IC258 the output of which is connected, respectively, to one of the two inputs of each of the IC's 261 to 268. Pins 6, 4, 2 and 15 of IC255 are connected to the respective second inputs of IC264 to IC261. Pins 6, 4, 2 and 15 of IC256 are connected to the respective second inputs of IC264 to IC261.

In the embodiment of FIG. 13, operating program storage 19 comprises the circuit elements IC259, IC260, IC269, IC270 and the resistors R271 to R279. Element IC260 is an RCA type 4040 counter. Elements IC269 and IC270 each comprise an RCA type 4066 analog switch.

Pin 10 of IC260 is connected to an input E414 which is in turn connected to output A414 of rotary position indicator 3. Pin 11 of IC260 is connected to an input E415 leading to output A406 of precompression stroke indicator 5, 6, 7. Pins 12 and 14 of IC260 are connected to the two inputs of IC259. The output of IC259 is connected to the second input of IC258. Pins 9, 7, 6, 5, 3, 2, 4 and 13 of IC260 are connected to the respective second inputs of IC268 to IC261. The outputs of IC268 to IC265 are respectively connected to pins 13, 12, 5 and 6 of IC269. The outputs of IC264 to IC261 are respectively connected to pins 12, 6, 5 and 13 of IC270. Pins 1, 4, 7, 8 and 11 of IC269 and IC270 have supplied thereto a voltage of −12 V. Pins 14 of IC269 and IC270 are commonly connected to an input E421 and to an output A431. Input E421 leads to output A420 of compression computer 21. Output A431 leads to input E433 of multiplier 22. Pins 2, 10, 3 and 9 of IC269 are connected, via resistors R279 to R276 to output A430. Similarly, pins 10, 9, 3 and 2 of IC270 are connected to output A430 through resistors R275 to R272. Output A430 leads to input E432 of multiplier 22. Output A430 has supplied thereto, through resistor R271, a voltage of −12 V.

Figure 14:
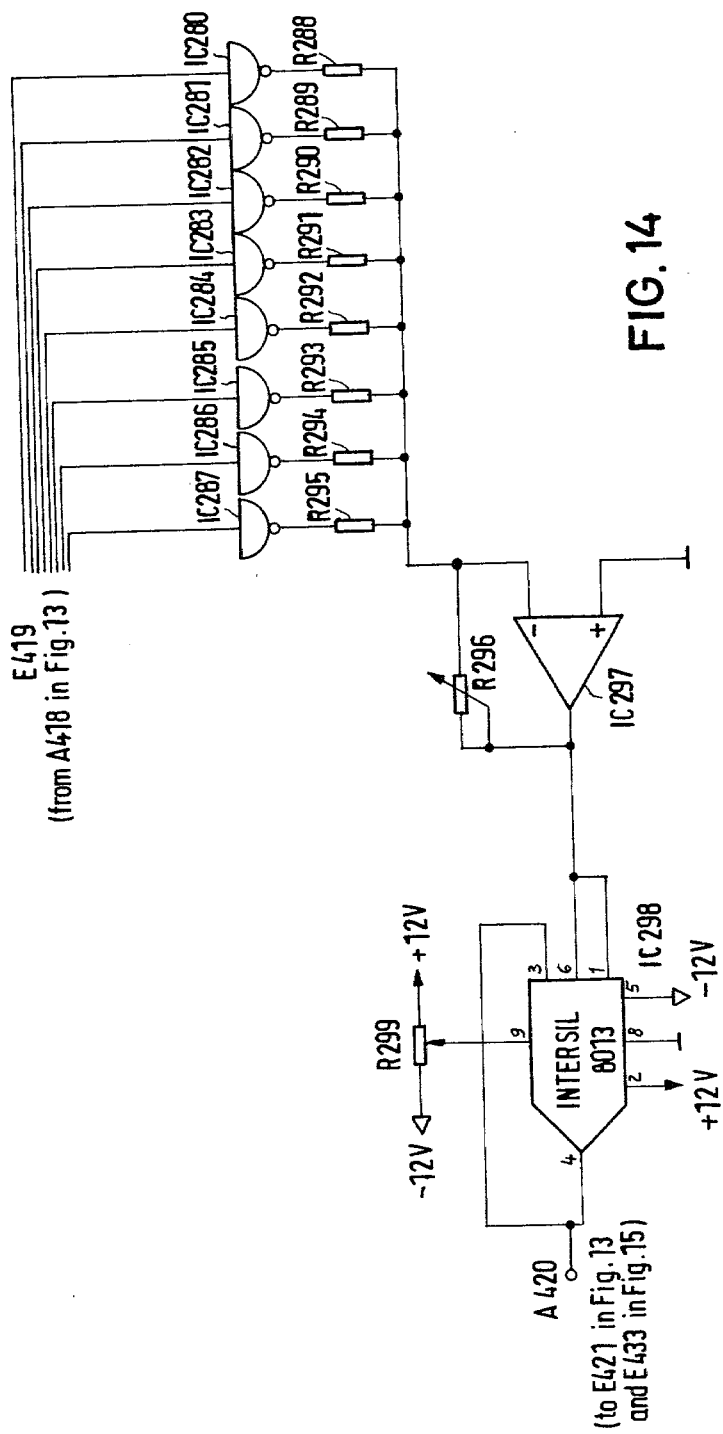
FIG. 14 is the wiring diagram of the compression computer.

FIG. 14 shows an embodiment of compression computer 21. A plurality of input lines E419 connected to operating program selector 19 serve to supply the compression computer with input signals delivered by the operating program selector. Each of the input lines E419 is connected to the input of the associated one of a plurality of inverters IC280 to IC287. The outputs of said inverters are each connected, via one of a plurality of resistors R288 to R295, to the negative input of an operational amplifier IC297. The positive input of IC297 is grounded. A feedback connection including a potentiometer R296 extends between the output of IC297 and the negative input thereof. The output of IC297 is further connected to pin 6 of circuit element IC298 which is an Intersil type 8013 analog multiplier as manufactured by the U.S. company Intersil of 10710 North Tantau Avenue, Cupertino, Calif. 95014. Pins 3 and 4 of IC298 are interconnected. Also interconnected are pins 1 and 6 thereof. Pin 5 has a voltage of −12 V supplied thereto. Pin 8 is grounded. Pin 2 has a voltage of +12 V supplied thereto. Pin 9 is connected to the center tap of a potentiometer R299 to the terminals of which a voltage of +12 V and −12 V is respectively applied. Pin 4 is connected to an output A420 leading to input E421 of operating program storage 20 and to input E433 of multiplier 22.

Figure 15:
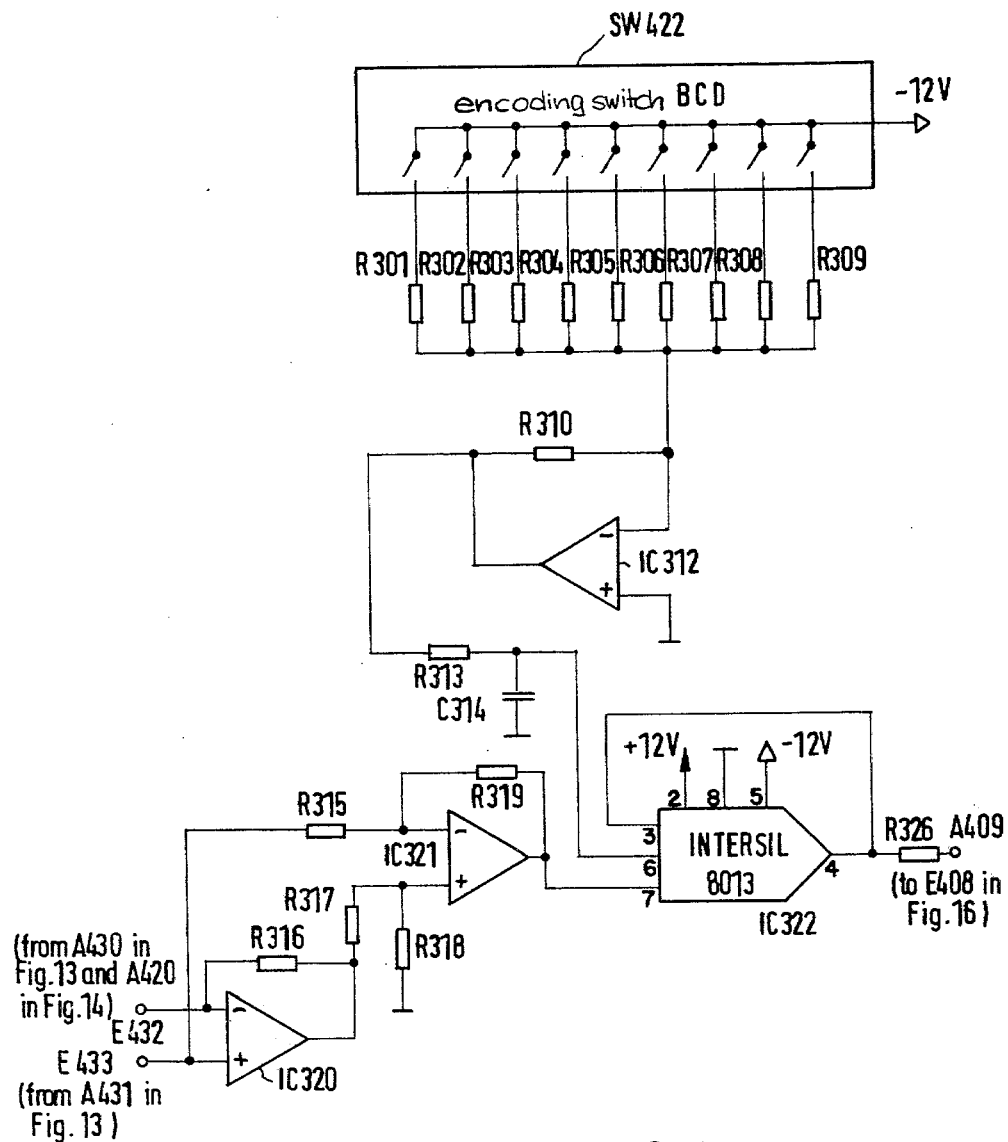
FIG. 15 is the wiring diagram of the delivery rate preselector and the multiplier.

FIG. 15 shows the wiring diagram of an embodiment of delivery rate preselector 24 and multiplier 22. Delivery rate preselector 24 comprises an encoding switch SW422, resistors R301 to R310 and an operational amplifier IC312. Encoding switch SW422 is a BCD-coded preselector switch. Its current supply line has a voltage of −12 V applied thereto. The taps of encoding switch SW411 are connected, via resistors R301 to R309 to the negative input of operational amplifier IC312, the output of which is connected, through resistor R310, to the negative input of the amplifier to establish a feedback connection. The positive input of operational amplifier IC312 is grounded.

Multiplier 22 comprises an analog multiplier IC322, two operational amplifiers IC320 and IC321, resistors R313, R315 to R319 and R326 and a capacitor C314. From the output of operational amplifier IC312 forming part of delivery rate preselector 24, a delivery rate preselecting signal is supplied to pin 6 of IC322 via a screening unit comprising R313 and C314. Pin 3 is connected to pin 4. Pin 2 has a voltage of +12 V supplied thereto. Pin 8 is grounded, and pin 5 has a voltage of −12 V supplied thereto. Pin 4 is connected, via resistor R326, to an output A409 leading to input E408 of four-quadrant motor driver 23. Pin 7 is connected to the output of operational amplifier IC321, which output is connected for feedback to the negative input thereof via resistor R319. In addition, the negative input of IC321 is connected, through resistor R315, to the positive input of operational amplifier IC320. Resistor R316 provides a feedback connection between the output of IC320 and the negative input thereof. Besides that, the output of IC320 is connected, through resistor R317, to the positive input of IC321. The positive input of IC321 is also grounded through resistor R318. The negative input of IC320 is connected to an input terminal E432 leading to output terminal A430 of operating program storage 20. The positive input of IC320 is connected to an input terminal E433 leading to output terminal A431 of operating program storage 20 and to output terminal A420 of compression computer 21.

Figure 16:
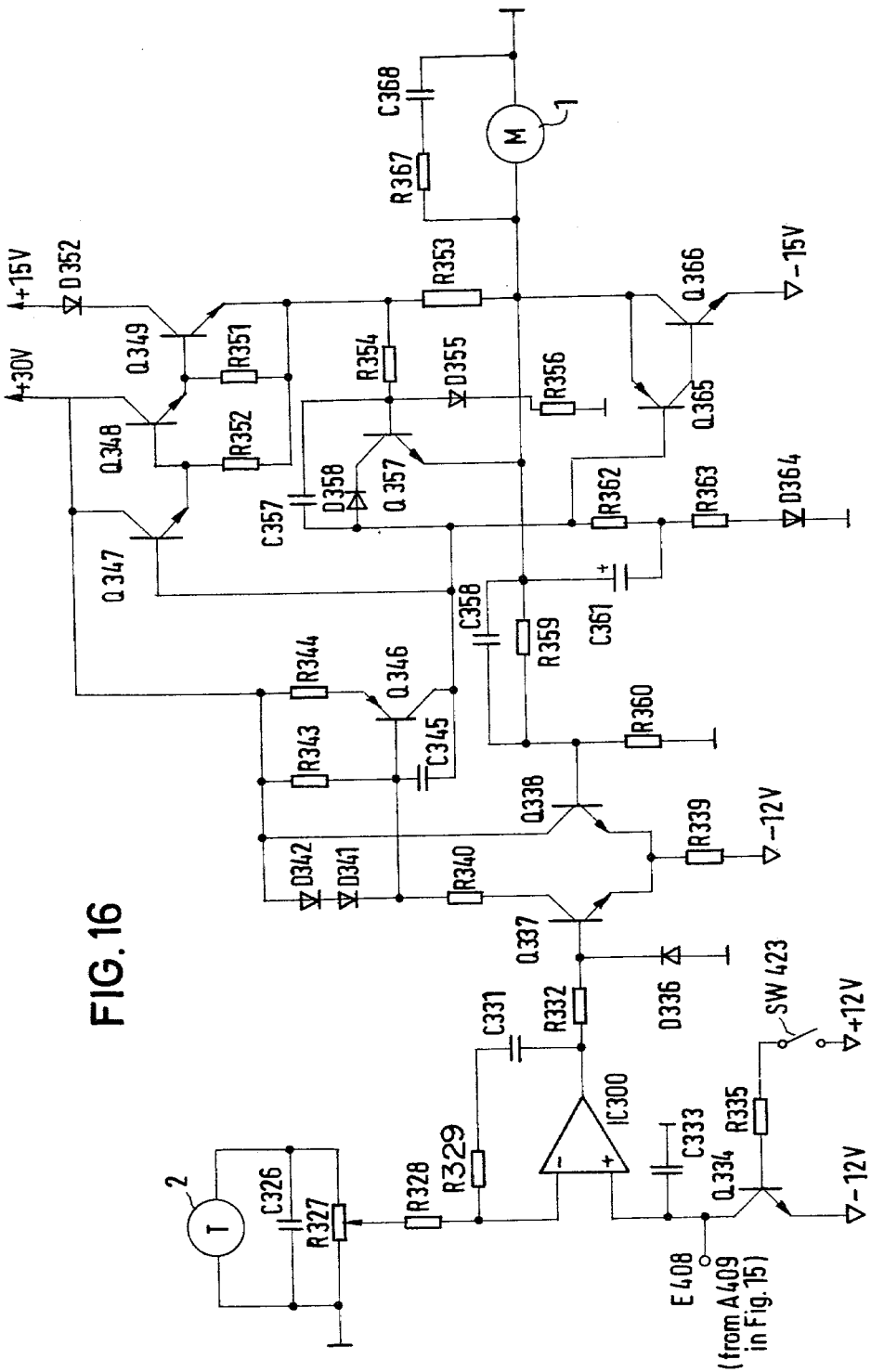
FIG. 16 is the wiring diagram of a four-quadrant motor driver.

FIG. 16 shows the wiring diagram of an embodiment of four-quadrant motor driver 23 the input terminal E408 of which has an input signal supplied thereto from output terminal A409 of multiplier 22. This input signal is received by the positive input of operational amplifier IC300, this input terminal being grounded via a capacitor C333. The said positive input is also connected to the collector of a transistor Q334 the emitter of which has a voltage of −12 V supplied thereto. A voltage of +12 V is applied to the base of transistor Q334 via a resistor R335 and a switch SW423. Upon switch SW423 being closed, the four-quadrant motor driver will receive a stop signal causing motor 1 to be stopped.

A resistor R329 and a capacitor R331 form a feedback connection between the output of IC300 and the negative input thereof.

The negative input of IC300 is also connected, via a resistor R328, to the center tap of a potentiometer R327, one terminal of which is grounded and, in addition, connected to one terminal of tachometer generator 2. The other side of R327 is connected to the second terminal of tachometer generator 2. In addition, a capacitor C326 is connected across resistor R327.

The output of operational amplifier IC300 is connected, via resistor R332, to the base of transistor Q337 which base is grounded via diode D336. The emitter of Q337 is connected to the emitter of another transistor Q338, a voltage of −12 V being applied to both emitters via resistor R339. The collector of Q337 has a voltage of +30 V applied thereto via a resistor R340 and two series-connected diodes D341 and D342. The collector of Q338 is directly connected to the +30 V terminal. The base of Q338 is grounded through resistor R360. In addition, the base of Q338 is connected, via resistor R359, to one terminal of motor 1, the other terminal of which is grounded. A capacitor C358 is connected across resistor R359. Connected across the terminals of motor 1 is a series connection comprising a resistor R367 and a capacitor C368.

A voltage applied to motor 1 through a transistor Q366 of which the emitter has a voltage of −15 V applied thereto and the collector of which is connected to one terminal of motor 1. The collector of Q366 is connected to the emitter of a transistor Q365 the collector of which is connected to the base of Q366. The base of Q365 is connected to the collector of Q366 through a resistor R362 having a capacitor C361 series-connected therewith. The junction between C361 and R362 is grounded by means of a resistor R363 connected in series with a diode D364.

The junction between R340 and D341 is connected to the base of a transistor Q346 whose collector is connected to the base of a transistor Q347. The collector of Q346 is connected to the base of this transistor through a feedback capacitor C345. A voltage of +30 V is applied to the emitter of Q346 via a resistor R344. A voltage of +30 V is also applied to the base of Q346 via a resistor R343. In addition, the collector of Q346 is connected to the base of Q365.

A voltage of +30 V is applied to the collector of Q347. The emitter of Q347 is connected to the base of transistor Q348. A voltage of +30 V is applied to the collector of Q348. The emitter of Q348 is connected to the base of a transistor Q349 to the collector of which a voltage of +15 V is applied through a diode D350. The collector of Q349 is connected to the cathode of D350. A resistor R351 forms a feedback connection between the emitter and the basis of Q349, another feedback connection extending via resistor R352 to the base of transistor Q348. In addition, the emitter of Q349 is connected to motor 1 through a resistor R353. The emitter of Q359 is also connected, via a resistor R354, to the base of a transistor Q357 whose emitter is connected to motor 1. A feedback connection between the collector and the base of Q357 is formed by a diode D358 connected in series with a capacitor C357. The cathode of D358 is connected to the collector of Q357. The collector of Q346 is connected to the junction between D358 and C357. The base of Q357 is grounded through a diode D355 connected in series with a resistor R356. The anode of D355 is connected to the base of Q357.

Motor 1 is a motor of known construction having a bell type armature of particularly low inertia permitting the motor to be rapidly accelerated and stopped again. The motor operates at an average speed of 4500 rpm.

The four-quadrant motor driver 23, employing the control signals it receives from multiplier 22, produces the current required for the operation of motor 1. It enables the motor to be driven in a forward direction as well as in a reverse direction and to be both braked and accelerated in both directions of rotation. Detailed information on the motor will be found in the Engineering Handbook by Electro-Craft Corporation, 1600 Second Street South, Hopkins, Minn. 55343, titled "DC Speed Controls Servo Systems."

Gearbox 4 has a reduction ratio of 75:1, so that cam plate 8 will rotate at a speed of approximately one revolution per second.

Figure 9:
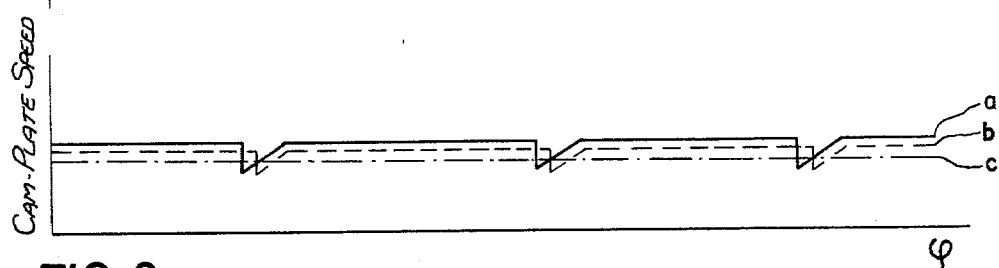
FIG. 9 is a diagram showing the relationship between the speed of the cam plate and the angle of rotation of the cam plate existing in cases of compressible fluids to be delivered against pressures higher than atmospheric pressures.

All of the operating programs stored in operating program storage 20 have the basic shape shown in FIG. 9 and differ only in respect of the depth and length of the sawtooth-shaped valleys.

What is claimed is:

1. A reciprocating piston pump for the pulsation-free delivery of a fluid with the use of at least two cylinders connected parallel on their discharge side, of which one in each instance sucks and the other delivers, in which the pistons working in said cylinders are controlled by a cam plate driven by rotary drive means, and in which each piston, for the purpose of compensating for the compressibility of the fluid, is caused to perform a precompression stroke following a shortened suction stroke wherein, during said precompression stroke, the piston speed is initially increased abruptly and then declines again until the end of the precompression stroke, characterized in that the length of the precompression stroke has a constant value, that the rotary speed of said drive means is reduced to a lower value at the beginning of fluid delivery and is restored to its normal value by the end of the precompression stroke.

2. The reciprocating piston pump of claim 1, characterized in that the rotary speed of the drive means is reduced, throughout the sequence of events, in proportion to the additional amount of fluid delivered as a result of precompression.

3. The reciprocating piston pump of claim 1 or 2, characterized in that said precompression-stroke indicator comprises a signaling element attached to said cam plate and a sensor co-operating with said signaling element.

4. The reciprocating piston pump of claim 1 or 2, characterized in that the rotary speed of the rotary drive means is uniformly increased again to its normal value up to the end of the precompression stroke.

5. The reciprocating piston pump of claim 1 or 2, characterized in that said cam plate is a double-grooved cam plate and that the grooves of the cam plate co-operate in a positive manner with cam followers associated therewith.

6. The reciprocating piston pump of claim 1 or 2, characterized by the provision of a precompression-stroke indicator adapted to indicate the beginning of the precompression stroke, of an angular-position indicator adapted to indicate the momentary rotary position of said cam plate, of a pulsation discriminator connected to a pressure measuring instrument and adapted to determine whether a pressure pulse is due to overcompensation or undercompensation, and of an operating program storage for said drive means, said storage having stored therein a plurality of operating programs, each of said programs being adapted, as regards different predetermined rotary positions of said cam plate between the beginning and the end of the precompression stroke, to establish a corresponding different pattern of a reduced operating speed of said cam plate between the predetermined rotary position selected therefor and the end of the precompression stroke, and of an operating program selector coupled to said pulsation discriminator and adapted, depending on whether said pulsation discriminator indicates overcompensation or undercompensation, to cause said operating program storage to activate an operating program according to which said associated predetermined rotary position is spaced by a smaller or larger amount, respectively, from the beginning of the precompression stroke than in the case of the previously selected operating program.

7. The reciprocating piston pump of claim 6, characterized in that there is connected, between the rotary drive means for said cam plate and said operating program storage, a compression computer adapted to receive the selected operating program from said operating program storage and adapted to receive, from said precompression-stroke indicator, via said pulsation discriminator and said operating program selector, information as to the distance between the beginning of the precompression stroke and the beginning of fluid delivery, and that said compression computer is adapted, taking into consideration predetermined parameters of the reciprocating piston pump inputted thereto, proportionally to reduce, throughout the sequence of events, the rotary speed predetermined by the selected operating program.

8. The reciprocating piston pump of claim 7, characterized in that there is connected, between said compression computer and said rotary drive means, a multiplier adapted to multiply the operating program, as modified by said compression computer, by a factor which is capable of being selected by means of a delivery-rate preselector.

9. The reciprocating piston pump of claim 8, characterized in that said rotary drive means comprises an electric motor to which is coupled a tachometer generator which is adapted to produce an actual-value signal to be transmitted to a servo controller adapted to control said electric motor, said servo controller receiving its desired-value signal from said multiplier.

* * * * *